United States Patent [19]

Lautenschläger et al.

[11] 4,377,695

[45] Mar. 22, 1983

[54] ω-(2-OXO-BENZAZOLINYL)-ALKANOIC ACID DERIVATIVES

[75] Inventors: Hans-Heiner Lautenschläger, Pulheim-Stommeln; Hans Betzing, Kerpen-Horrem; Brigitte Stoll, Pulheim; Manfred Probst, Frechen, all of Fed. Rep. of Germany

[73] Assignee: A. Nattermann & Cie GmbH, Cologne, Fed. Rep. of Germany

[21] Appl. No.: 318,963

[22] Filed: Nov. 6, 1981

[30] Foreign Application Priority Data

Nov. 11, 1980 [DE] Fed. Rep. of Germany ....... 3042481

[51] Int. Cl.³ .............. C07D 263/54; C07D 235/04; C07D 277/62
[52] U.S. Cl. ............................ 548/305; 548/170; 548/230
[58] Field of Search ......................... 548/305

[56] References Cited

U.S. PATENT DOCUMENTS 4,161,603 7/1979 Habermeier ........................ 548/305
4,209,527 6/1980 Sarges .................................. 548/305

FOREIGN PATENT DOCUMENTS 2935902 2/1981 Fed. Rep. of Germany ...... 548/230
48-28916 5/1973 Japan ................................... 548/305
48-28917 5/1973 Japan ................................... 548/305

OTHER PUBLICATIONS

A. Nattermann & Cie GmbH, Derwent Abstract, DE2950478, 6-19-81.
A. Nattermann & Cie GmbH, Derwent Abstract, DE2934746.

Primary Examiner—Donald G. Daus
Assistant Examiner—Sharon A. Gibson
Attorney, Agent, or Firm—Pearne, Gordon, Sessions, McCoy & Granger

[57] ABSTRACT

The present invention refers to new ω-(2-oxo-benzazolinyl)-alkanoic acids as well as salts and esters thereof having the general formula I

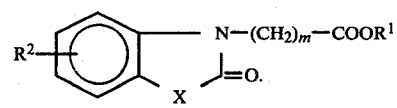

and having antiinflammatory, analgesic and antithrombotic activity.

15 Claims, No Drawings

ω-(2-OXO-BENZAZOLINYL)-ALKANOIC ACID DERIVATIVES

As described in three own prior, non-published German patent applications P 29 34 746.4, P 29 50 478.7 and P 29 35 902.2, ω-(2-oxo-4-imidazolin-1-yl)-alkanoic acids and ω-(2-oxo-4-oxazolin-3-yl)-alkanoic acids as well as salts and esters thereof have valuable pharmacological properties such as antithrombotic, antiarteriosklerotic, antiinflammatory and analgetic properties. They furthermore are useful in combination with antikoagulantia, in particular with heparin and heparinates.

It has now been found that the ω-(2-oxo-benzazolinyl)-alkanoic acids according to the present invention as well as their salts and esters having the general formula I represent valuable active agents for drugs. Thus, the present invention refers to the new compounds of the general formula I

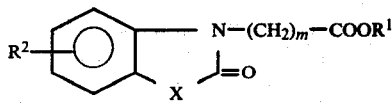

wherein
m is an integer from 6 to 10, preferably 6 to 8,
$R^1$ is hydrogen, an alkali ion or a straight or branched hydrocarbon group having from 1 to 6 carbon atoms,
X is an oxygen atom, a sulphur atom or a $NR^3$-group, $R^3$ being H, —$(CH_2)_n$—$R^4$ with n being an integer from 0 to 7 and R being a methyl group, the unsubstituted phenyl group or the substituted phenyl group

and X being preferably the $NR^3$-group,
$R^2$ and $R^5$ which may be identical or different from each other represent hydrogen, halogen, the methyl, the trifluoromethyl, the methoxy, the nitro or an amino group.

The present invention furthermore refers to process for producing the same and to pharmaceutical compounds comprising the same.

The new compounds show interesting pharmacological properties such as antiallergic, antiasthmatic, antiarteriosklerotic and antiinflammatory properties. They furthermore have an excellent compatibility by the stomach and, therefor, may be in particularly used for the treatment of allergic, asthmatic, thrombotic and arteriosklerotic diseases with at the same time favourable gastrointestinal properties. The compounds of the general formula I have a low toxicity. They therefor are important for the treatment both of human beings and such diseases in human beings.

The new ω-(2-oxo-benzazolinyl)-alkanoic acid derivatives may be used in the form of the free acids or as salts with pharmacologically compatible bases or in the form of their esters as active ingredients in drugs together with usual carrier materials or diluents. The compound are used in daily dosages ranging from 0.1 to 100 mg./kg.

The compounds according to the present invention are produced in manners known per se in that a benzazolin-2-one of the general formula II

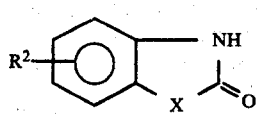

wherein $R^2$ and X have the same meaning as in formula I, is reacted with an alkylating agent of the general formula III $$Z—(CH_2)_m—COOR^1 \quad \text{III}$$

wherein m and $R^1$ have the same meaning as in formula I and Z is a halogen atom in an organic solvent such as acetone, methylethylketone, dimethylformamide, with the addition of an auxiliary base such as sodium hydride, possibly in the presence of an alkali metal iodide as catalyst.

Thereafter, the esters of formula I wherein $R^1$ is $C_{1-6}$-alkyl may be converted in manners known per se into an alkali metal salt of the general formula I wherein $R^1$ is an alkali metal, for instance by reaction with an alkali metal hydroxide in aqueous, alcoholic or alcoholic-ethereal solvents and into an acid of the general formula I with $R^1$ being hydrogen by subsequent addition of a mineral acid. Vice versa, an acid of the general formula I with $R^1$ being hydrogen and the alkali metal salts of the general formula I with $R^1$ being an alkali metal may be converted into an ester of the general formula I with $R^1$ being $C_{1-6}$ alkyl in manners know per se, for instance by subjecting an acid of the general formula I with $R^1$ being hydrogen to reaction with a solution of hydrochloric acid in the respective alcohol or by subjecting an acid or a salt thereof of the general formula I with $R^1$ being hydrogen or, respectively, an alkali metal ion, to reaction with thionylchloride and subjecting the resulting acid chloride to reaction with the respective alcohol.

The products of formula I wherein X is $NR^3$, $R^3$ being the —$(CH_2)_n$—$R^4$—group, $R^4$ having the same meaning as in formula I, may also be produced in that an ω-(2-oxo-benzazolinyl)-alkanoic acid or their derivative of formula I wherein X is $NR^3$ and $R^3$ is hydrogen, to reaction with an alkylating agent of formula IV $$Y—(CH_2)_n—R^4 \quad \text{IV}$$

wherein Y is halogen and n and $R^4$ have the same meaning as in formula I. Y may also be another usual and favourable group to be split off, for instance the azide group —$N_2$ or the radical of a sulphuric acid ester in particular of a sulphuric acid lower alkyl ester.

The compounds of formula I, wherein $R^2$ is $NH_2$, may be also be produced in usual manners from the corresponding compounds of formula I wherein $R^2$ is $NO_2$, by reduction, for instance with hydrogen, an alkali metal dithionite or other reducing agents.

Starting materials of formula II may for instance be: benzoxazolin-2-one, benzthioazolin-2-one, benzimidazolin-2-one and their derivatives substituted in 4-, 5-, 6- and 7-position by F, Cl, Br, $CH_3$, $CF_3$, $CH_3O$, $NO_2$ and $NH_2$ as well as the corresponding benzimidazolin-2-ones further substituted in the 1-position by $R^3$.

$R^3$ preferably represent straight hydrocarbon groups having from 1 to 8 carbon atoms (n=0 to 7, $R^4$=methyl), the unsubstituted phenyl group and the phenyl groups substituted in the 2-, 3- or 4-position by F, Cl, Br, $CH_3$, $CF_3$, $CH_3O$, $NO_2$ and $NH_2$ as well as the corresponding aralkyl groups for instance the unsubstituted benzyl- and phenylethyl group and such groups substituted as herein above given.

Alkylating agents of formula III may be the following ω-halogenoalkanoic acids: the 7-chloro, the 7-bromo and the 7-iodoenanthic acid, the 8-chloro-, the 8-bromo- and the 8-iodocaprylic acid, the 9-chloro-, the 9-bromo- and the 9-iodopelargonic acid, the 10-chloro-, the 10-bromo- and the 10-iodocaprinic acid, the 11-chloro-, the 11-bromo- and the 11-iodoundecanoic acid.

Suitable alkylating agents according to formula IV are for instance: diazomethane, dimethylsulfate, chloro-, bromo- and iodomethane, chloro-, bromo- and iodoethane, 3-chloro-, 3-bromo- and 3-iodopropane, 4-chloro-, 4-bromo- and 4-iodobutane, 5-chloro-, 5-bromo- and 5-iodopentane, 6-chloro-, 6-bromo- and 6-iodohexane, 7-chloro-, 7-bromo- and 7-iodoheptane, 8-chloro-, 8-bromo- and 8-iodooctane, benzylchloride, benzylbromide, benzyliodide as well as the corresponding benzylhalides substituted by F, Cl, Br, $CH_3$, $CF_3$, $CH_3O$, $NO_2$ and/or $NH_2$, phenylethylchloride, phenylethylbromide, phenylethyliodide as well as the corresponding phenylethylhalides substituted by F, Cl, Br, $CH_3$, $CF_3$, $CH_3O$, $NO_2$ and/or $NH_2$. The unsubstituted and correspondingly in the phenyl group substituted 3-phenylpropyl-, 4-phenylbutyl-, 5-phenylpentyl-, 6-phenylhexyl-, 7-phenylheptyl- and 8-phenyloctylhalides.

The alcohols $R^1OH$ preferably are such which are straight or secondary branched saturated alcohols with 1 to 6 carbon atoms such as methanol, ethanol, propanol, isopropanol, butanol, pentanol, hexanol.

The new compounds of formula I may be administered for instance orally, by injection or rectally as pharmaceutical products which may be solid or liquid, in the form of suspensions or solutions. Such products are for instance tablets, powders, capsules, granules, ampoules, syrups and suppositories.

The production of the compounds according to the present invention is further illustrated by the follow examples.

The reported melting points have been measured on a Büchi 510 melting point apparatus, are given in °C. and are not corrected. The reaction time is given in hours (h). The IR-Spektra have been registered with a Perkin-Elmer 257 and the mass spektra with a Varian MAT-311-A (70 eV).

EXAMPLE 1

7-(2-Oxo-benzoxazolin-3-yl)-enanthic acid ethyl ester 3.0 g. of sodium hydride (80% suspension in mineral oil) are washed with n-pentane and added to a mixture of 13.5 g. of benzoxazolin-2-one and 200 cc. of anhydrous dimethylformamide (DMF). The mixture is stirred at room temperature and towards end of hydrogen formation at 60° C. Thereafter, 19.3 g. of 7-chloroenanthic acid ethyl ester and 3.0 g. of sodium iodide (NaJ) are added thereto and the mixture is heated to 80° C. for 8 hours. After cooling to room temperature, the mixture is diluted with water and extracted with chloroform ($CHCl_3$). The extract are consequetively washed with water, with 5% $NaHCO_3$-solution and another time with water. The extract is dried over $Na_2SO_4$, the solvent is distilled off in a vacuum and the residue is further purified chromatographically on silicic acid using chloroform as eluant.

Yield: 23.4 g. (oil). IR (film): 1780 and 1735 $cm^{-1}$.

EXAMPLE 2

8-(2-Oxo-benzoxazolin-3-yl)-caprylic acid methyl ester

The product is produced as described in example 1 from 3.0 g. of NaH (80% suspension in mineral oil), 13.5 g. of benzoxazolin-2-one, 200 cc. of DMF, 23.7 g. of 8-bromocaprylic acid ethyl ester and 3.0 g. of NaJ. Eluant in chromatographic purification: hexane/ethyl acetate.

Yield: 20 g. Fp.: 47° C. IR (in KBr): 1780 and 1740 $cm^{-1}$.

EXAMPLE 3

8-(5-Nitro-2-oxo-benzoxazolin-3-yl)-caprylic acid methyl ester

The product is produced as described in example 1 from 6 g. of NaH (80% suspension in mineral oil), 36 g. of 5-nitrobenzoxazolin-2-one (produced in usual manner by reacting 2-amino-4-nitrophenol-hydrochloride with phosgene), 400 cc. of DMF, 47.4 g. of 8-bromo caprylic acid methyl ester and 6 g. of NaJ.

Yield: 25 g. Fp.: 50° to 51° C. IR (film): 1780 and 1730 $cm^{-1}$.

EXAMPLE 4

8-(5-Amino-2-oxo-benzoxazolin-3-yl)-caprylic acid methyl ester 6.7 g. of 8-(5-Nitro-2-oxo-benzoxazolin-3-yl)-caprylic acid methyl ester are dissolved in 100 cc. of methanol and the solution is heated to boiling. 20 cc. of water are added to the solution and within 1 hour 13.9 g. of sodium dithionite are added and the mixture is boiled so long until the starting yellow solution is decolourized. Thereafter, the solution is evaporated in a vacuum, the residue is stirred with dilute soda lye and the solid crude product as filtered off with suction. The crude product is washed with water, dried and further purified chromatographically on silicic acid using hexane/ethyl acetate as eluant.

Yield: 0.5 g. Fp.: 88° to 90° C. IR (in KBr): 1755 (broad) with shoulders 1740 $cm^{-1}$.

EXAMPLE 5

8-(6-Methyl-2-oxo-benzoxazolin-3-yl)-caprylic acid methyl ester

The product is produced as described in example 1 from 3.6 g. of NaH (of 80% suspension in mineral oil), 19.9 g. of 6-methylbenzoxazolin-2-one (produced in usual manners by subjecting 2-amino-5-methyl-phenol-hydrochloride to reaction with phosgene), 240 cc. of DMF, 28.4 g. of 8-bromo caprylic acid methyl ester and 3.6 g. NaJ.

Yield: 31.1 g. (oil). IR (film): 1780 and 1740 $cm^{-1}$.

EXAMPLE 6

8-(5-Chloro-2-oxo-benzoxazolin-3-yl)-caprylic acid methyl ester

The product is produced as described in example 1 from 3 g. of NaH (80% suspension in mineral oil), 17 g.

of 5-chloro-benzoxazolin-2-one (produced in usual manners by subjecting 2-amino-4-chloro-phenol-hydrochloride to reaction with phosgene), 200 cc. of DMF, 23.7 g. of 8-bromo-caprylic acid methyl ester and 3 g. of NaJ.

Yield: 24 g. Fp.: 54° to 56° C. IR (in KBr): 1780 and 1735 cm$^{-1}$.

EXAMPLE 7

8-(2-Oxo-benzthiazolin-3-yl)-caprylic acid methyl ester

The product is produced as described in example 1 from 3 g. of NaH (80% suspension in mineral oil), 15.1 g. of benzthiazolin-2-one, 200 cc. of DMF, 23.7 g. of 8-bromo-caprylic acid methyl ester and 3 g. NaJ.

Yield: 26.6 g. (oil). IR (film): 1740 and 1685 cm$^{-1}$.

EXAMPLE 8

8-(2-Oxo-benzimidazolin-1-yl)-caprylic acid methyl ester

The product is produced as described in example 1 from 2.8 g. of NaH (80% suspension in mineral oil), 25 g. of benzimidazolin-2-one, 180 cc. of DMF, 22.1 g. of 8-bromocaprylic acid methyl ester and 2.8 g. of NaJ. Eluant in chromatographic purification: chloroform/methanol.

Yield: 12 g. Fp.: 88° C. IR (in KBr): 1740 and 1700 cm$^{-1}$.

EXAMPLE 9

8-(3-Octyl-2-oxo-benzimidazolin-1-yl)-caprylic acid methyl ester

The product is produced as described in example 1 from 0.9 g. of NaH (80% suspension in mineral oil), 7.5 g. of 1-octylbenzimidazolin-2-one (produced) by alkylation from benzimidazolin-2-one with bromooctane according to example 8), 100 cc. of DMF, 7.1 g. of 8-bromocaprylic acid methyl ester and 0.9 g. of NaJ. Eluant in chromatographic purification: hexane/ethylacetate.

Yield: 6.4 g. (oil). IR (film): 1740 and 1705 cm$^{-1}$.

EXAMPLE 10

7-(2-Oxo-3-phenyl-benzimidazolin-1-yl)-enanthic acid ethyl ester

The product is produced as described in example 1 from 1.9 g. of NaH (80% suspension in mineral oil), 13.2 g. of 1-phenylbenzimidazolin-2-one (produced in usual manner by subjecting N-phenyl-o-phenylenediamine to reaction with phosgene), 120 cc. of DMF, 12.1 g. of 7-chloroenanthic acid ethyl ester and 1.9 g. of NaJ. Eluant in chromatographic purification: hexane/ethylacetate.

Yield: 16.5 g. (oil). IR (film): 1740 (shoulder) and 1720 cm$^{-1}$.

EXAMPLE 11

8-(2-Oxo-3-phenyl-benzimidazolin-1-yl)-caprylic acid methyl ester

The product is produced as described in example 1 from 2.4 g. of NaH (80% suspension in mineral oil), 16.8 g. of 1-phenylbenzimidazolin-2-one, 160 cc. of DMF, 19.0 g. of 8-bromocapyrlic acid methyl ester and 2.4 g. of NaJ. Eluant in chromatographic purification: hexane/ethylacetate.

Yield: 20 g. Fp.: 43° to 45° C. IR (film): 1740 (shoulder) and 1715 cm$^{-1}$.

EXAMPLE 12

11-(2-Oxo-3-phenyl-benzimidazolin-1-yl)-undecanoic acid methyl ester

The product is produced as described in example 1 from 1.3 g. of NaH (80% suspension in mineral oil), 10 g. of 1-phenylbenzimidazolin-2-one, 200 cc. of DMF, 13.3 g. of 11-bromoundecanoic acid methyl ester and 1.3 g. of NaJ. Eluant in chromatographic purification: hexane/ethylacetate.

Yield: 15.8 g. Fp.: 74° C. IR (in KBr): 1735 and 1705 cm$^{-1}$.

EXAMPLE 13

7-[3-(3-Chlorophenyl)-2-oxo-benzimidazolin-1-yl]-enanthic ethyl ester

The product is produced as described in example 1 from 1.2 g. of NaH (80% suspension in mineral oil), 9.8 g. of 1-(3-chlorophenyl)-benzimidazolin-2-one (produced in usual manners by subjecting N-(3-chlorophenyl)-o-phenylene diamine to reaction of phosgene), 80 cc. of DMF, 7.7 g. of 7-chloroenanthic acid ethyl ester and 1.2 g. of NaJ.

Yield: 9.1 g. (oil). IR (film): 1725 1725 cm$^{-1}$ (broad).

EXAMPLE 14

8-[3-(3-chlorophenyl)-2-oxo-benzimidazolin-1-yl]-caprylic acid methyl ester

The product is produces as described in example 1 from 1.2 g. of NaH (80% suspension in mineral oil), 9.8 g. of 1-(3-chlorophenyl)-benzimidazolin-2-one, 80 cc. of DMF, 9.5 g. of 8-bromocaprylic acid methyl ester and 1.2 g. of NaJ.

Yield: 9.5 g. Fp.: 40° to 42° C. IR (film): 1725 cm$^{-1}$ (broad).

EXAMPLE 15

8-(3-Benzyl-2-oxo-benzimidazolin-1-yl)-caprylic acid methyl ester

The product is produced as described in example 1 from 0.75 g. of NaH (80% suspension in mineral oil), 5.6 g. of 1-benzylbenzimidazolin-2-one (produced in usual manners by alkylation of benzimidazolin-2-one with benzylchloride according to example 8), 50 cc. of DMF, 5.9 g. of 8-bromocaprylic acid methyl ester and 0.75 g. of NaJ.

Yield: 4.1 g. (oil). IR (film): 1740 and 1710 cm$^{-1}$.

EXAMPLE 16

8-[3-(2-Chlorobenzyl)-2-oxo-benzimidazolin-1-yl]-caprylic acid methyl ester

The product is produced as described in example 1 from 0.72 g. of NaH (80% suspension in mineral oil), 7 g. of 8-(2-oxobenzimidazolin-1-yl)-caprylic acid methyl ester, 100 cc. of DMF, 3.9 g. of 2-chlorobenzylchloride and 0.72 g. of NaJ. Eluant of chromatographic purification: hexane/ethylacetate.

Yield: 6.4 g. (oil). IR (film): 1735 and 1700 cm$^{-1}$.

EXAMPLE 17

8-[3-(4-Chlorobenzyl)-2-oxo-benzimidazolin-1-yl]-caprylic acid methyl ester

The product is produced as described in example 1 from 0.72 g. of NaH (80% suspension in mineral oil), 7 g. of 8-(2-oxo-benzimidazolin-1-yl)-caprylic acid methyl ester, 100 cc. of DMF, 3.9 g. of 4-chlorobenzylchloride and 0.72 g. of NaJ Eluant in chromatographic purification: hexane/ethylacetate.

Yield: 4.8 g. Fp.: 88° C. IR (in KBr): 1735 and 1700 cm$^{-1}$.

EXAMPLE 18

8-[3-(4-Fluorobenzyl)-2-oxo-benzimidazolin-1-yl]-caprylic acid methyl ester

The product is produced as described in example 1 from 0.72 g. of NaH (80% suspension in mineral oil), 7 g. of 8-(2-oxo-benzimidazolin-1-yl)-caprylic acid methyl ester, 100 cc. of DMF, 3.5 g. of 4-fluorobenzylchloride and 0.72 g. of NaJ. Eluant for chromatographic purification: hexane/ethylacetate.

Yield: 7.5 g. Fp.: 48° C. IR (film): 1735 and 1700 cm$^{-1}$.

EXAMPLE 19

8-[3-(4-Methylbenzyl)-2-oxo-benzimidazolin-1-yl]-caprylic acid methyl ester

The product is produced as described in example 1 from 0.72 g of NaH (80% suspension in mineral oil), 7 g. of 8-(2-oxo-benzimidazolin-1-yl)-caprylic acid methyl ester, 100 cc. of DMF, 3.4 g. of 4-methylbenzylchloride and 0.72 g. of NaJ. Eluant for chromatographic purification: hexane/ethylacetate.

Yield: 7.3 g. Fp.: 70° C. IR (in KBr): 1740 and 1705 cm$^{-1}$.

EXAMPLE 20

8-[2-Oxo-3-(3-trifluoromethylbenzyl)-benzimidazolin-1-yl]-caprylic acid methyl ester The product is produced as described in example 1 from 0.72 g. of NaH (80% suspension in mineral oil), 7 g. of 8-(2-oxo-benzimidazolin-1-yl)-caprylic acid methyl ester, 100 cc. of DMF, 4.7 g. of 3-trifluoromethylbenzylchloride and 0.72 g. of NaJ. Eluant for chromatographic purification: hexane/ethylacetate.

Yield: 8.4 g. (oil). IR (film): 1740 and 1710 cm$^{-1}$.

EXAMPLE 21

8-[3-(4-Methoxyphenyl)-2-oxo-benzimidazolin-1-yl]-caprylic acid methyl ester

The product is produced as described in example 1 from 0.72 g. of NaH (80% suspension in mineral oil), 7 g. of 8-(2-oxo-benzimidazolin-1-yl)-caprylic acid methyl ester, 100 cc. of DMF, 3.8 g. of 4-methoxybenzylchloride and 0.72 g. of NaJ. Eluant for chromatographic purification: hexane/ethylacetate.

Yield: 7.2 g. (oil). IR (film): 1740 and 1710 cm$^{-1}$.

EXAMPLE 22

7-(2-Oxo-benzoxazolin-3-yl)-enanthic acid 18.4 g. of 7-(2-Oxobenzoxazolin-3-yl)-enanthic acid ethyl ester are dissolved in 60 cc. of methanol. 2.52 g. of sodium hydroxide are dissolved in methanol and added to the above solution. The mixture is stirred at room temperature for 24 hours, the solvent is distilled off and the residue is dissolved in water. The aqueous solution is shaken several times with chloroform, the chloroform solution is discarded. The aqueous phase is acidified with dilute hydrochloric acid and extracted with chloroform. The chloroform solution is washed with water and dried over Na$_2$SO$_4$. The solvent is distilled off and the residue is purified chromatographically on silicic acid gel using hexane/ethylacetate as eluant.

Yield: 4.75 g. Fp.: 89° C. MS [m/e]: 263 (93%), 148 (80%), 135 (100%).

EXAMPLE 23

8-(2-Oxo-benzoxazolin-3-yl)-caprylic acid

The product is produced as described in example 22 from 14.5 g. of 8-(2-oxo-benzoxazolin-3-yl)-caprylic acid methyl ester and 2.4 g. of NaOH. Eluant in chromatographic purification: chloroform.

Yield: 7.8 g. Fp.: 81° to 82° C. MS [m/e]: 277 (100%), 148 (80%9, 135 (99%).

EXAMPLE 24

8-(5-Nitro-2-oxo-benzoxazolin-3-yl)-caprylic acid

The product is produced as described in example 22 from 18.3 g. of 8-(5-nitro-2-oxo-benzoxazolin-3-yl)-caprylic acid methyl ester and 2.4 g. of NaOH. Eluant in chromatographic purification: chloroform.

Yield: 0.2 g. Fp.: 115° C. MS [m/e]: 322 (64%), 263 (24%), 193 (44%), 180 (18%), 98 (100%).

EXAMPLE 25

8-(6-Methyl-2-oxo-benzoxazolin-3-yl)-caprylic acid

The product is produced as described in example 22 from 31 g. of 8-(6-methyl-2-oxo-benzoxazolin-3-yl)-caprylic acid methyl ester and 4.4 g. of NaOH. Eluant in chromatographic purification: chloroform.

Yield: 11.9 g. Fp.: 90° to 91° C. MS [m/e]: 291 (100%), 162 (56%), 149 (89%).

EXAMPLE 26

8-(5-Chloro-2-oxo-benzoxazolin-3-yl)-caprylic acid

The product is produced as described in example 22 from 10.9 g. of 8-(5-chloro-2-oxo-benzoxazolin-3-yl)-caprylic acid methyl ester and 1.6 g. of NaOH. Eluant in chromatographic purification: chloroform.

Yield: 4.8 g. Fp.: 98° to 99° C. MS [m/e]: 311 (78%), 182 (55%), 169 (83%).

EXAMPLE 27

8-(2-Oxo-benzthiazolin-3-yl)-caprylic acid

The product is produced as described in example 22 from 20 g. of 8-(2-oxo-benzthiazolin-3-yl)-caprylic acid methyl ester and 2.6 g. of NaOH.

Yield: 7.8 g. Fp.: 86° C. MS [m/e]: 293 (100%), 165 (36%), 151 (96%).

EXAMPLE 28

8-(2-Oxo-benzimidazolin-1-yl)-caprylic acid

The product is produced as described in example 22 from 10 g. of 8-(2-oxo-benzimidazolin-1-yl)-caprylic acid methyl ester and 1.44 g. of NaOH.

Yield: 5.1 g. Fp.: 110° C. MS [m/e]: 276 (85%), 147 (100%), 134 (85%).

EXAMPLE 29

8-(3-Octyl-2-oxo-benzimidazolin-1-yl)-caprylic acid

The product is produced as described in example 22 from acid methyl ester and 0.6 g. of NaOH.

Yield: 0.53 g. Fp.: 85° C. MS [m/e]: 388 (100%), 329 (14%), 147 (17%).

EXAMPLE 30

7-(2-Oxo-3-phenyl-benzimidazolin-1-yl)-enanthic acid

The product is produced as described in example 22 from 16 g. of 7-(2-oxo-3-phenyl-benzimidazolin-1-yl)-enanthic acid ethyl ester and 2.1 g. of NaOH.

Yield: 12.6 g. Fp.: 111° to 112° C. MS [m/e]: 338 (100%), 223 (49%), 210 (48%).

EXAMPLE 31

8-(2-Oxo-3-phenyl-benzimidazolin-1-yl)-caprylic acid

The product is produced as described in example 22 from 15 g. of 8-(2-oxo-3-phenyl-benzimidazolin-1-yl)-caprylic acid methyl ester and 1.64 g. of NaOH.

Yield: 12.6 g. Fp.: 115° to 116° C. MS [m/e]: 353 (100%), 223 (35%), 210 (36%).

EXAMPLE 32

11-(2-Oxo-3-phenyl-benzimidazolin-1-yl)-undecanoic acid

The product is produced as described in example 22 from 11 g. of 11-(2-oxo-3-phenyl-benzimidazolin-1-yl)-undecanoic acid methyl ester and 1.2 g. of NaOH.

Yield: 10.8 g. Fp.: 120° C. MS [m/e]: 394 (100%), 223 (32%), 210 (34%).

EXAMPLE 33

7-[3-(3-Chlorophenyl)-2-oxo-benzimidazolin-1-yl]-enanthic acid

The product is produces as described in example 22 from 9 g. of 7-[3-(3-chlorophenyl)-2-oxo-benzimidazolin-1-yl]-enanthic acid ethyl ester and 1.76 g. of NaOH.

Yield: 5.4 g. Fp: 101° to 103° C. MS [m/e]: 372 (100%), 313 (41%), 257 (65%), 244 (61%).

EXAMPLE 34

8-[3-(3-Chlorophenyl)-2-oxo-benzimidazolin-1-yl]-caprylic acid

The product is produced as described in example 22 from 9.3 g. of 8-[3-(3-chlorophenyl)-2-oxo-benzimidazolin-1-yl]-caprylic acid methyl ester and 2.56 g. of NaOH.

Yield: 4.2 g. Fp: 98°-99° C. MS [m/e]: 386 (100%), 327 (13%), 257 (40%), 244 (38%).

EXAMPLE 35

8-(3-Benzyl-2-oxo-benzimidazolin-1-yl)-caprylic acid

The product is produced as described in example 22 from 4.3 g. of 8-(3-benzyl-2-oxo-benzimidazolin-1-yl)-caprylic acid methyl ester and 0.5 g. of sodium hydroxide.

Yield: 2.7 g. Fp.: 100° to 101° C. MS [m/e]: 366 (72%), 237 (17%), 224 (28%), 91 (100%).

EXAMPLE 36

8-[3-(2-Chlorobenzyl)-2-oxo-benzimidazolin-1-yl]-caprylic acid

The product is produced as described in example 22 from 6.4 g. of 8-[3-(2-chlorobenzyl)-2-oxo-benzimidazolin-1-yl]-caprylic acid methyl ester and 1.2 g. of sodium hydroxide.

Yield: 5.8 g. Fp: 118° C. MS [m/e]: 400 (64%), 365 (100%), 271 (10%), 258 (9%), 125 (68%).

EXAMPLE 37

8-[3-(4-Chlorobenzyl)-2-oxo-benzimidazolin-1-yl]-caprylic acid

The product is produced as described in example 22 from 4 g. 8-[3-(4-chlorobenzyl)-2-oxo-benzimidazolin-1-yl]-caprylic acid methyl ester and 0.8 g. of NaOH.

Yield: 3.5 g. Fp.: 123° C. MS [m/e]: 400 (100%), 271 (8%), 258 (13%), 125 (91%).

EXAMPLE 38

8-[3-(4-Fluorobenzyl)-2-oxo-benzimidazolin-1-yl]-caprylic acid

The product is produced as described in example 22 from 7.5 g. of 8-[3-(4-fluorobenzyl)-2-oxo-benzimidazolin-1-yl]-caprylic acid methyl ester and 1.5 g. of NaOH.

Yield: 6 g. Fp.: 112° to 114° C. MS [m/e]: 384 (82%), 255 (8%), 242 (14%), 109 (100%).

EXAMPLE 39

8-[3-(4-Methylbenzyl)-2-oxo-benzimidazolin-1-yl]-caprylic acid

The product is produced as described in example 22 from 7.3 g. of 8-[3-(4-methylbenzyl)-2-oxo-benzimidazolin-1-yl]-caprylic acid methyl ester and 1.5 g. of NaOH.

Yield: 6.5 g Fp.: 109° to 113° C. MS [m/e]: 380 (76%), 252 (3%), 238 (6%), 105 (100%).

EXAMPLE 40

8-[2-Oxo-3-(3-trifluoromethylbenzyl)-benzimidazolin-1-yl]-caprylic acid

The product is produced as described in example 22 from 5.7 g. of 8-[2-oxo-3-(3-trifluoromethylbenzyl)-benzimidazolin-1-yl]-caprylic acid methyl ester and 1.5 g. of NaOH.

Yield: 5.7 g. Fp.: 109° to 111° C. MS [m/e]: 434 (100%), 305 (22%), 292 (25%), 159 (61%).

EXAMPLE 41

8-[3-(4-Methoxybenzyl)-2-oxo-benzimidazolin-1-yl]-caprylic acid

The product is produced as described in example 22 from 7 g. of 8-[3-(4-methoxybenzyl)-2-oxo-benzimidazolin-1-yl]-caprylic acid methyl ester and 1.4 g. of NaOH. Recrystallization from ether.

Yield: 4.7 g. Fp.: 106° to 108° C. MS [m/e]: 396 (24%), 254 (0,7%), 121 (100%).

EXAMPLE 42

7-(2-Oxo-benzoxazolin-3-yl)-enanthic acid sodium salt 7-(2-Oxo-benzoxazolin-3-yl)-enanthic acid is dissolved in ethanol and neutralized with alcoholic soda lye. The mixture is evaporated to dryness in a vacuum and the solid residue is pulverized.

IR (in KBr): 1760 and 1565 cm$^{-1}$.

As described in Example 42, the following sodium salts are produced (Examples 43 to 61).

EXAMPLE 43

8-(2-Oxo-benzoxazolin-3-yl)-caprylic acid sodium salt

IR (in KBr): 1770 and 1565 cm$^{-1}$.

EXAMPLE 44

8-(5-Nitro-2-oxo-benzoxazolin-3-yl)-caprylic acid sodium salt

IR (in KBr): 1770 and 1565 cm$^{-1}$.

EXAMPLE 45

8-(6-Methyl-2-oxo-benzoxazolin-3-yl)-caprylic acid sodium salt

IR (in KBr): 1770 and 1565 cm$^{-1}$.

EXAMPLE 46

8-(5-Chloro-2-oxo-benzoxazolin-3-yl)-caprylic acid sodium salt

IR (in KBr): 1780 and 1565 cm$^{-1}$.

EXAMPLE 47

8-(2-Oxo-benzthiazolin-3-yl)-caprylic acid sodium salt

IR (in KBr): 1680 and 1565 cm$^{-1}$.

EXAMPLE 48

8-(2-Oxo-benzimidazolin-1-yl)-caprylic acid sodium salt

IR (in KBr): 1720 and 1575 cm$^{-1}$.

EXAMPLE 49

8-(3-Octyl-2-oxo-benzimidazolin-1-yl)-caprylic acid sodium salt

IR (in KBr): 1710 and 1565 cm$^{-1}$.

EXAMPLE 50

7-(2-Oxo-3-phenyl-benzimidazolin-1-yl)-enanthic acid sodium salt

IR (in KBr): 1710 and 1565 cm$^{-1}$.

EXAMPLE 51

8-(2-Oxo-3-phenyl-benzimidazolin-1-yl)-caprylic acid sodium salt

IR (in KBr): 1710 and 1570 cm$^{-1}$.

EXAMPLE 52

11-(2-Oxo-3-phenyl-benzimidazolin-1-yl)-undecanoic sodium salt

IR (in KBr): 1715 and 1565 cm$^{-1}$.

EXAMPLE 53

7-[3-(3-Chlorophenyl)-2-oxo-benzimidazolin-1-yl]-enanthic acid sodium salt

IR (in KBr): 1715 and 1565 cm$^{-1}$.

EXAMPLE 54

8-[3-(3-Chlorophenyl)-2-oxo-benzimidazolin-1-yl]-caprylic acid sodium salt

IR (in KBr): 1715 and 1565 cm$^{-1}$.

EXAMPLE 55

8-(3-Benzyl-2-oxo-benzimidazolin-1-yl)-caprylic acid sodium salt

IR (in KBr): 1705 and 1565 cm$^{-1}$.

EXAMPLE 56

8-[3-(2-Chlorobenzyl)-2-oxo-benzimidazolin-1-yl]-caprylic acid sodium salt

IR (in KBr): 1710 and 1570 cm$^{-1}$.

EXAMPLE 57

8-[3-(4-Chlorobenzyl)-2-oxo-benzimidazolin-1-yl]-caprylic acid sodium salt

IR (in KBr): 1710 and 1580 cm$^{-1}$.

EXAMPLE 58

8-[3-(4-Fluorobenzyl)-2-oxo-benzimidazolin-1-yl]-caprylic acid sodium salt

IR (in KBr): 1710 and 1565 cm$^{-1}$.

EXAMPLE 59

8-[3-(4-Methylbenzyl)-2-oxo-benzimidazolin-1-yl]-caprylic acid sodium salt

IR (in KBr): 1710 and 1565 cm$^{-1}$.

EXAMPLE 60

8-[2-Oxo-3-(3-trifluoromethylbenzyl)-benzimidazolin-1-yl]-caprylic acid sodium salt IR (in KBr): 1710 and 1565 cm$^{-1}$.

EXAMPLE 61

8-[3-(4-Methoxybenzyl)-2-oxo-benzimidazolin-1-yl]-caprylic acid sodium salt

IR (in KBr): 1710 and 1565 cm$^{-1}$.

EXAMPLE 62

8-(2-Oxo-3-phenyl-benzimidazolin-1-yl)-caprylic acid hexylester 5 cc. of thionylchloride are added to 1 g. of 8-(2-oxo-3-phenyl-benzimidazolin-1-yl)-caprylic acid and the mixture is stirred at room temperature for 2 hours. Unreacted thionylchloride is evaporated in a vacuum, the residue is dissolved in a small amount of anhydrous chloroform and 238 mg. of hexanol are added to the solution. The mixture is stirred at room temperature for 4 hours, consequetively washed with 5% NaHCO$_3$ solution and water, dried over Na$_2$SO$_4$ and evaporated in a vacuum. The residue is further purified chromatographically on silicic acid gel using hexane/ethyl acetate as eluant.

Yield: 500 mg. (oil). MS [m/e]: 436 (100%), 335 (20%), 223 (38%), 210 (37%).

As described in example 62 or by reaction of the ω-(2-oxo-benzazolinyl)-alkanoic acids with solutions of hydrochloric acid in alcohols (as described in the examples of German patent applications P 29 34 746.4, P 29 35 902.2 and P 29 50 478.7) all esters claimed in claim 1 may be produced.

What we claim is:

1. ω-(2-Oxo-benzazolinyl)-alkanoic acids of formula I

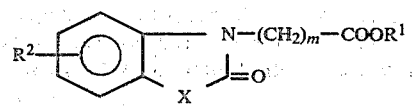

wherein m is an integer ranging from 6 to 10

R¹ is hydrogen, an alkali metal ion or a straight or branched hydrocarbon group having from 1 to 6 carbon atoms, X is a NR³-group, R³ representing —H, —(CH₂)ₙ—R⁴ with n being an integer from 0 to 7 and R⁴ being a methyl group, the unsubstituted phenyl group or the substituted phenyl group

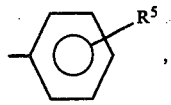

R² and R⁵ which may be identical or different from each other, represent hydrogen, halogen, a methyl, a trifluoromethyl, a methoxy, a nitro or an amino group.

2. 8-(2-Oxo-benzimidazolin-1-yl)-caprylic acid and their pharmacologically compatible salts and esters.

3. 8-(3-Octyl-2-oxo-benzimidazolin-1-yl)-caprylic acid and their pharmacologically compatible salts and esters.

4. 7-(2-Oxo-3-phenyl-benzamidazolin-1-yl)-enanthic acid and their pharmacologically compatible salts and esters.

5. 8-(2-Oxo-3-phenyl-benzimidazolin-1-yl)-caprylic acid and their pharmacologically compatible salts and esters.

6. 11-(2-Oxo-3-phenyl-benzimidazolin-1-yl)-undecanoic acid and their pharmacologically compatible salts and esters.

7. 7-[3-(3-Chlorophenyl)-2-oxo-benzimidazolin-1-yl]-enanthic acid and their pharmacologically compatible salts and esters.

8. 8-[3-(3-Chlorophenyl)-2-oxo-benzimidazolin-1-yl]-caprylic acid and their pharmacologically compatible salts and ester.

9. 8-(3-Benzyl-2-oxo-benzimidazolin-1-yl)-caprylic acid and their pharmacologically compatible salts and esters.

10. 8-[3-(2-Chlorobenzyl)-2-oxo-benzimidazolin-1-yl]-caprylic acid and their pharmacologically compatible salts and esters.

11. 8-[3-(4-Chlorobenzyl)-2-oxo-benzimidazolin-1-yl]-caprylic acid and their pharmacologically compatible salts and esters.

12. 8-[3-(4-Fluorobenzyl)-2-oxo-benzimidazolin-1-yl]-caprylic acid and their pharmacologically compatible salts and esters.

13. 8-[3-(4-Methylbenzyl)-2-oxo-benzimidazolin-1-yl]-caprylic acid and their pharmacologically compatible salts and esters.

14. 8-[2-Oxo-3-(3-trifluoromethylbenzyl)-benzimidazolin-1-yl]-caprylic acid and their pharmacologically compatible salts and esters.

15. 8-[3-(4-Methoxybenzyl)-2-oxo-benzimidazolin-1-yl]-caprylic acid and their pharmacologically compatible salts and esters.

* * * * *

UNITED STATES PATENT AND TRADEMARK OFFICE
CERTIFICATE OF CORRECTION

PATENT NO. : 4,377,695
DATED : March 22, 1983
INVENTOR(S) : Hans-Heiner Lautenschlager et al.

It is certified that error appears in the above—identified patent and that said Letters Patent is hereby corrected as shown below:

Column 1, line 13, delete "heparin" and substitute therefor --haparine--;

Column 1, line 35, delete "R" and substitute therefor --$R^4$--;

Column 5, line 35, delete the ")" after --produced--;

Column 6, line 25, delete "1725" (first occurrence);

Column 6, line 31, delete "produces" and substitute therefor --produced--;

Column 8, line 14, delete "(80%9," and substitute therefor --(80%),--;

Column 9, line 33, delete "produces"and substitute --produced--;

Column 10, line 53, delete "0,7%" and substitute therefor --0.7%--; and

Column 12, line 45, delete "consequetively" and substitute therefor --consecutively--.

Signed and Sealed this

Seventeenth Day of April 1984

[SEAL]

Attest:

GERALD J. MOSSINGHOFF

Attesting Officer    Commissioner of Patents and Trademarks